(12) United States Patent
Tani et al.

(10) Patent No.: US 9,308,109 B2
(45) Date of Patent: Apr. 12, 2016

(54) STENT GRAFT DELIVERY DEVICE

(71) Applicant: TERUMO KABUSHIKI KAISHA, Tokyo (JP)

(72) Inventors: Kazuyoshi Tani, Kawasaki (JP); Akira Sawada, Minamiashigara (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 86 days.

(21) Appl. No.: 14/338,769

(22) Filed: Jul. 23, 2014

(65) Prior Publication Data

US 2014/0336744 A1   Nov. 13, 2014

Related U.S. Application Data

(63) Continuation of application No. PCT/JP2012/079219, filed on Nov. 12, 2012.

(30) Foreign Application Priority Data

Feb. 24, 2012  (JP) .................................. 2012-038874

(51) Int. Cl.
| | |
|---|---|
| *A61F 2/06* | (2013.01) |
| *A61F 2/966* | (2013.01) |
| *A61F 2/07* | (2013.01) |
| *A61F 2/95* | (2013.01) |

(52) U.S. Cl.
CPC . *A61F 2/966* (2013.01); *A61F 2/07* (2013.01); *A61F 2002/9517* (2013.01)

(58) Field of Classification Search
CPC .... A61F 2002/9517; A61F 2/966; A61F 2/95
USPC ...................................... 623/1.11, 1.12, 1.23
See application file for complete search history.

(56) References Cited

U.S. PATENT DOCUMENTS

| | | | |
|---|---|---|---|
| 2008/0109065 | A1 | 5/2008 | Bowe |
| 2009/0157162 | A1 | 6/2009 | Chow et al. |
| 2011/0054585 | A1 | 3/2011 | Osborne |
| 2011/0301685 | A1 | 12/2011 | Kao |

(Continued)

FOREIGN PATENT DOCUMENTS

| | | |
|---|---|---|
| JP | 2009-521281 A | 6/2009 |
| JP | 2010-504821 A | 2/2010 |

(Continued)

OTHER PUBLICATIONS

Extended European Search Report dated Sep. 22, 2015, issued by the European Patent Office in the corresponding European Application No. 12869401.5. (4 pages).

(Continued)

*Primary Examiner* — Katherine M Shi

(74) *Attorney, Agent, or Firm* — Buchanan Ingersoll & Rooney PC

(57) ABSTRACT

The stent graft delivery device includes a shaft on which the stent graft is placed on the distal side; a sheath which is slidable outside of the shaft; a handle which is provided on the proximal side of the shaft and the sheath; and an operation unit which is provided with a switch mechanism. When a rotating member is rotated, while in a state of pressing a switch member of the switch mechanism inward, the sheath moves backward and the shaft moves forward using the handle as a reference.

20 Claims, 8 Drawing Sheets

(56) References Cited

U.S. PATENT DOCUMENTS

2011/0307049 A1* 12/2011 Kao .............................. 623/1.11
2012/0296409 A1    11/2012 Kawakita

FOREIGN PATENT DOCUMENTS

WO    WO 97/48350 A1    12/1997
WO    2009/124124 A1    10/2009
WO    2011/081007 A1    7/2011

OTHER PUBLICATIONS

International Search Report (PCT/ISA/210) mailed on Feb. 12, 2013, by the Japanese Patent Office as the International Searching Authority for International Application No. PCT/JP2012/079219.

* cited by examiner

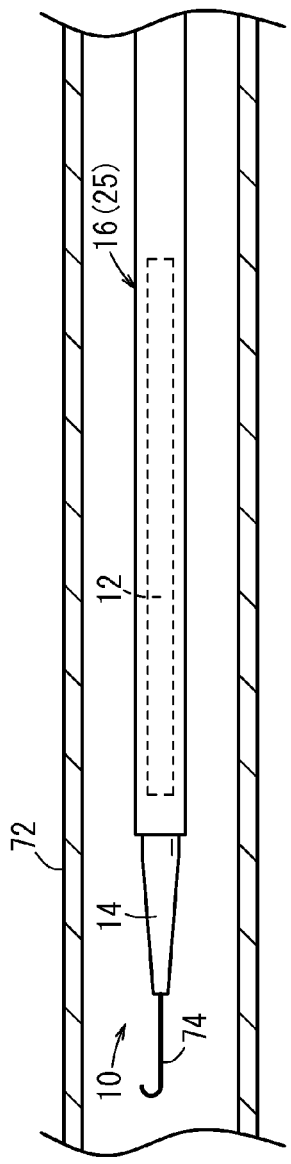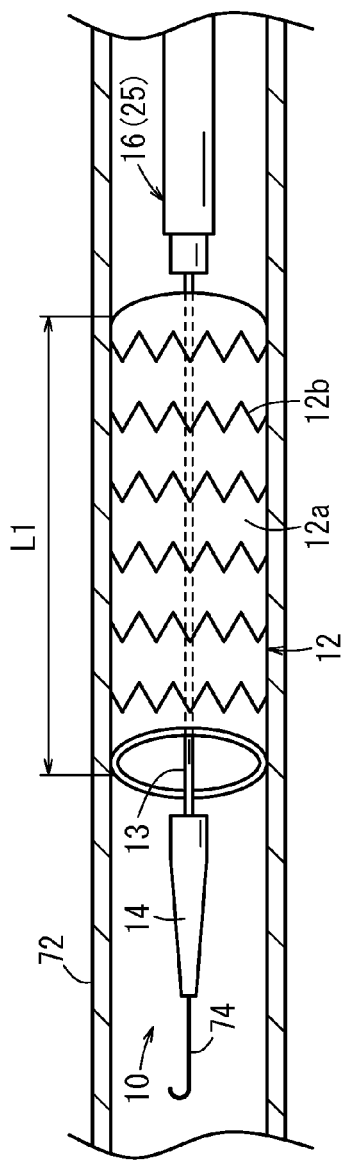
FIG. 6A
FIG. 6B

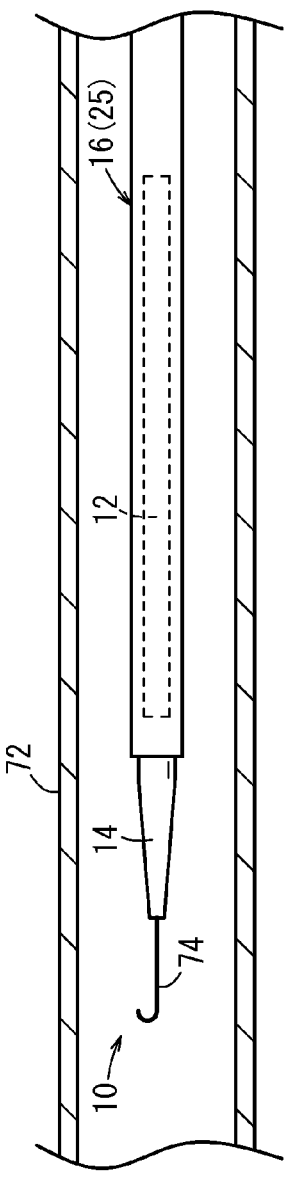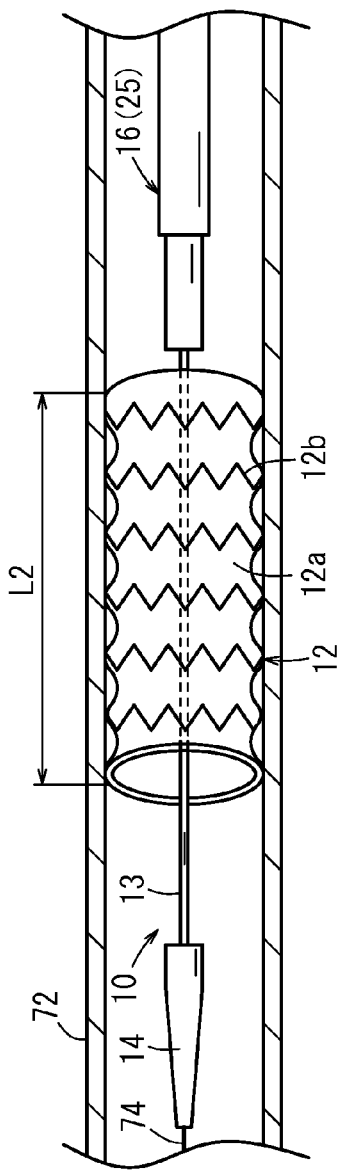
FIG. 7A
FIG. 7B

STENT GRAFT DELIVERY DEVICE

CROSS REFERENCES TO RELATED APPLICATIONS

This application is a continuation of International Application No. PCT/JP2012/079219 filed on Nov. 12, 2012, and claims priority to Japanese Application No. 2012-038874 filed on Feb. 24, 2012, the entire content of both of which is incorporated herein by reference.

TECHNICAL FIELD

The present invention relates to a stent graft delivery device which delivers a stent graft providing a metal skeleton (frame) in a tubular graft to a body cavity, and more specifically, to a stent graft delivery device for deploying a stent graft at a length different from the original length.

BACKGROUND DISCUSSION

In the related prior art, surgical operations using artificial blood vessels for treatments of an aortic aneurysm or aortic dissection have been performed, but a low invasive treatment using a stent graft has been widely performed in recent years (for example, see WO97/048350). A general stent graft is formed by suturing and fixing a skeleton (stent) in which a wire such as a nickel titanium alloy or stainless steel is formed in a Z shape or a ring shape to an inner surface or an outer surface of a tube (graft) which is formed of a cloth (fabric) woven by threads of a resin such as a polyester in a cylindrical shape, and is indwelled in a desired blood vessel by being deployed and expanded in a body cavity.

For example, in a case where a treatment for an aortic aneurysm is performed with a stent graft, it is required for both ends thereof to be indwelled in a normal blood vessel in the vicinity of a pathological blood vessel. Accordingly, a necessary minimum indwelling length required for a stent graft treatment becomes the length between normal blood vessels located in front and back of the pathological blood vessel. In general, the placement position or a necessary length of a stent graft is predicted from an X-ray contrast image or a CT image acquired before a surgery. But since it is difficult to predict the placement position or the necessary length, the predicted length does not always reach the necessary indwelling length and thus a new stent graft is required to be additionally inserted so that both of the ends thereof indwell in a blood vessel having a plurality of bent sections. Further, in a case where an aneurysm generated in a bent section of a blood vessel is treated with an indwelling stent graft, there is a possibility that the bent section in the blood vessel is distorted in a process of recovery and both of the ends of the indwelling stent graft fall out.

As a method for solving the above-described problem, it has been considered to use a stent graft which is longer than the necessary length for indwelling and to indwell the stent graft while it is being contracted in the length direction as needed. The stent graft is contracted and the entire length thereof is shortened by an operator pushing up the entire delivery device while gradually deploying the stent graft from the central side thereof by lowering a sheath accommodating the stent graft which is arranged on the outer surface of a shaft.

However, such a method depends on the expertise and/or technique of an operator, so there is a possibility that a graft is turned over or skeletons (frames) overlap each other when the degree of pushing up the delivery device is great, for example.

SUMMARY

The disclosure herein provides a stent graft delivery device capable of easily deploying a stent graft at a length different from the original length without depending on the technique of an operator.

An exemplary embodiment of a stent graft delivery device includes a stent graft; a shaft on which the stent graft is placed; a tubular sheath which is slidable in an axial direction with respect to the shaft and capable of accommodating the stent graft; a handle which is provided on a proximal side of the shaft and the sheath; an operation unit which is movably provided in the axial direction with respect to the shaft, in a position separated from the handle in the axial direction, and which drives at least the sheath from among the shaft and the sheath; and a switch mechanism which is provided in the operation unit, in which the shaft and the sheath are provided and which is movable in the axial direction using the handle as a reference. Due to the action of the switch mechanism, the operation unit may switch states between a first state in which only the sheath from among the shaft and the sheath is allowed to be moved in the axial direction with respect to the handle while being operated by the operation unit and a second state in which the shaft and the sheath are allowed to be moved in directions opposite to each other with respect to the handle while being operated by the operation unit due to the action of the switch mechanism.

According to the aforesaid exemplary configuration of the disclosure, only the sheath from among the shaft and the sheath is moved in the proximal direction with respect to the handle and thus the stent graft may be deployed at the original length in a living body lumen by operating the operation unit when in the first state as set by the switch mechanism. In contrast, the sheath is moved in the proximal direction with respect to the handle and the shaft is moved in the distal direction with respect to the handle, and thus the stent graft in the living body lumen may be deployed to be shorter than the original length by operating the operation unit when in the second state as set by the switch mechanism. In such a manner, since the first state and the second state may be switched between each other by the switch mechanism, the size of the stent graft to be contracted is easily adjusted and the stent graft may be indwelled in a blood vessel at an arbitrary (desired) length which is shorter than the original length, depending on the length or meandering degree of a blood vessel of a patient. Hence, when compared with the technique of shortening the entire length of the stent graft by pushing up the entire stent graft delivery device as in the prior art, the disclosure here provides a technique of easily shortening the entire length of the stent graft with less dependence on the expertise and/or technique of the operator.

In the aforesaid exemplary embodiment of the stent graft delivery device according to the disclosure, the operation unit includes a rotating member which is rotatable with respect to the shaft and the sheath and which is connected to the sheath, and a guide member which is connected in a rotatable manner with respect to the rotating member and which is not rotatable relative to the shaft, wherein the shaft and the sheath are not rotatable relative to one another. An end of a flexible linear member is wound around the rotating member, another end of the linear member is fixed to the handle, and the guide member may guide a middle portion of the linear member between a portion wound around the rotating member and a portion fixed by the handle.

According to the aforesaid exemplary configuration, the linear member is wound around the rotating member along with the rotation operation, so the operation unit is drawn toward the handle side, and thus the sheath may be reliably moved in the proximal direction.

Further, in the aforesaid stent graft delivery device, the rotating member includes an outer cylindrical portion and a bobbin portion which is provided in the outer cylindrical portion and which has the linear member wound around it, and the guide member may be arranged so as to cover the bobbin portion in the outer cylindrical portion.

In addition, according to the aforesaid exemplary embodiment, since the guide member is provided in the rotating member, the operation unit may be formed in a compact manner.

In the exemplary embodiment of the stent graft delivery device according to the disclosure, the guide member is provided with a guide hole in which one end is open at a site facing the bobbin portion in an inner peripheral portion of the guide member and another end is open on the proximal surface of the guide member such that the middle portion of the linear member may be slidably guided by the guide hole.

Thus, according to the aforesaid exemplary configuration, it is possible for the linear member to be appropriately guided from the handle side to bobbin portion side.

In the exemplary embodiment of the stent graft delivery device according to the disclosure, a first biasing member may be provided which biases the operation unit in a direction separating the operation unit from the handle.

According to the above configuration, since tension strength is applied to the linear member in a state in which a biasing force of the first biasing member is acted, the distance between the handle and the operation unit may be reliably held at the distance prescribed by the linear member.

Further, in the aforesaid stent graft delivery device, one end of the first biasing member may be attached to the proximal surface of the guide member and another end may be attached to the distal surface of the handle.

Hence, according to the aforesaid configuration, since the first biasing member is arranged between the guide member and the handle which are not rotatable relative to each other, the first biasing member is not twisted even when the rotating member is operated.

In the aforesaid stent graft delivery device, a spiral groove may be formed in the outer peripheral portion of the shaft, and the switch mechanism may include a switch member which is displaceable between a position engaged with the spiral groove and a position separated from the spiral groove.

According to the aforesaid configuration, a feed screw mechanism is formed by the switch member and the spiral groove and the sheath may be reliably moved in the axial direction with respect to the handle by operating the rotating member to be rotated in a state in which the switch member and the spiral groove are engaged with each other.

In the aforesaid stent graft delivery device, the switch mechanism includes a second biasing member which biases the switch member in a direction separating the switch member from the spiral groove, and the switch member may be engaged with the spiral groove when a pushing operation is performed on the switch member.

According to the aforesaid configuration, since the operation unit maintains the first state when the switch member is not pushed and the operation unit enters the second state only when the switch member is operated (pushed in), switching between the first state and the second state may be smoothly performed.

In the aforesaid stent graft delivery device, the shaft is provided with a slit-shaped or a groove-shaped guide unit which intersects the spiral groove and extends in the axial direction. A plurality of the switch members may be provided in the circumferential direction in the operation unit at intervals.

According to the aforesaid exemplary configuration, since another guide member is necessarily engaged with the spiral groove even when any one of the switch members is in the position to be inserted into the guide unit while the rotating member is operated to rotate in a state in which the switch member and the spiral groove are engaged with each other, the shaft may be smoothly moved forward by the rotation operation of the rotating member, so the operability thereof is excellent.

Further, in the aforesaid stent graft delivery device, relative displacement resistance between the handle and the shaft may be greater than friction resistance between the sheath and the stent graft.

According to the exemplary embodiment of the disclosure, it is possible to prevent the shaft from moving in the proximal direction together with the sheath when the sheath is allowed to be moved in the proximal direction with respect to the handle.

More particularly, in the aforesaid stent graft delivery device, an intermediate member may be included in which one end is fixed to the guide member and another end is slidably inserted into the handle, and a displacement restricting mechanism may be included which allows the intermediate member to be displaced in the proximal direction with respect to the handle and inhibits the intermediate member from being displaced in the distal direction with respect to the handle.

According to the aforesaid exemplary configuration, it is possible to prevent the sheath from moving in the distal direction with respect to the handle.

In the aforesaid exemplary stent graft delivery device, the displacement restricting mechanism may include a restriction release unit which releases displacement restriction with respect to the intermediate member.

According to the aforesaid configuration, it is possible for the sheath to move in the distal direction with respect to the handle as needed.

Further, according to an exemplary embodiment of the stent graft delivery device of the disclosure, the stent graft may be easily deployed at a length different from the original length without depending on the technique of an operator.

BRIEF DESCRIPTION OF DRAWINGS

FIG. 6A is a first view describing an operation which deploys the stent graft at the original length, and FIG. 6B is a second view describing an operation which deploys the stent graft at the original length.

FIG. 7A is a first view describing an operation which deploys the stent graft at a length shorter than the original length, and FIG. 7B is a second view describing an operation which deploys the stent graft at a length shorter than the original length.

DETAILED DESCRIPTION

Hereinafter, a stent graft delivery device 10 according to the disclosure here will be described with reference to preferred exemplary embodiments and the accompanying drawings.

Figure 1:
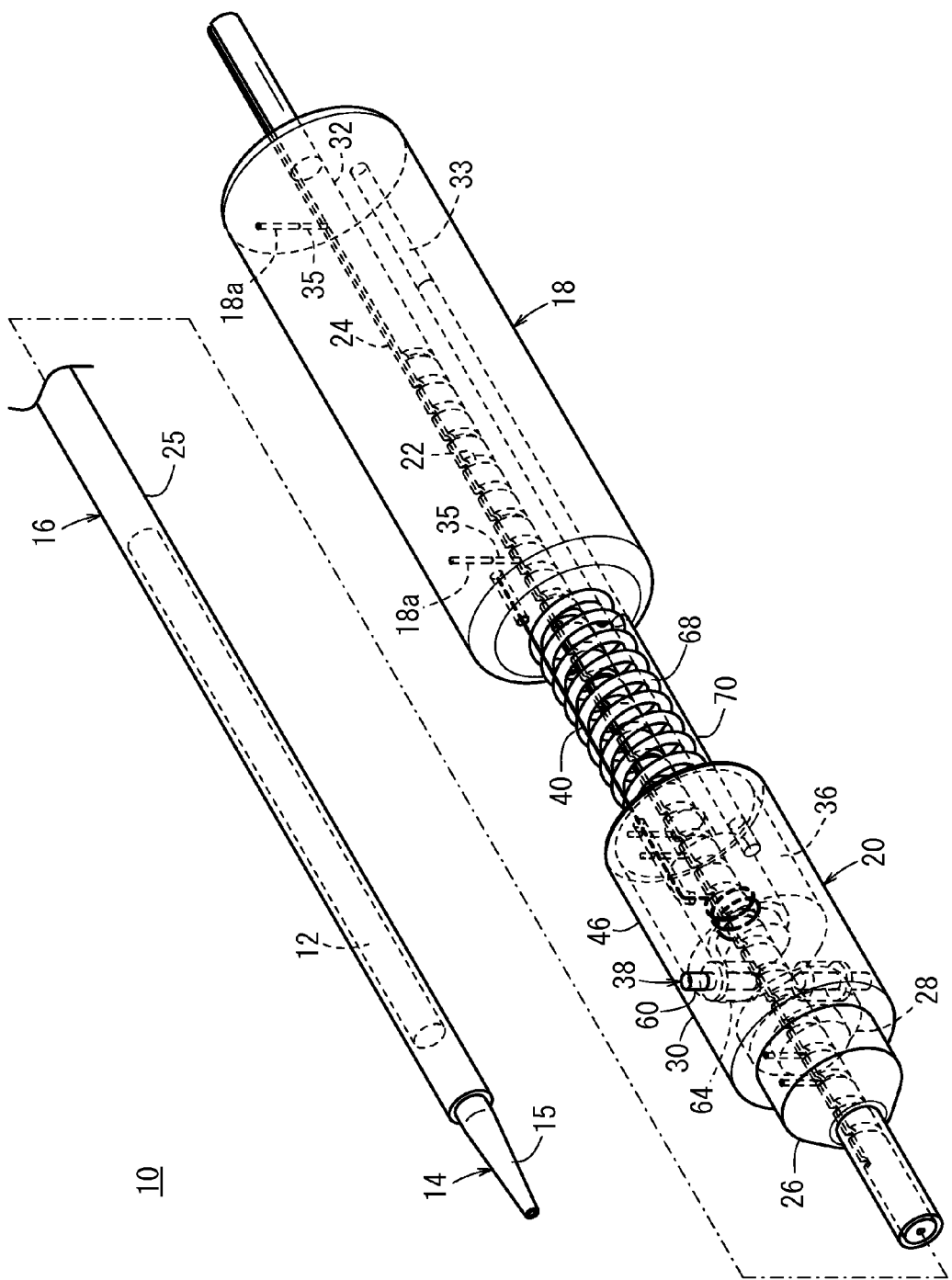
FIG. 1 is a partially omitted perspective view illustrating a stent graft delivery device according to an exemplary embodiment of the disclosure herein.
Figure 2:
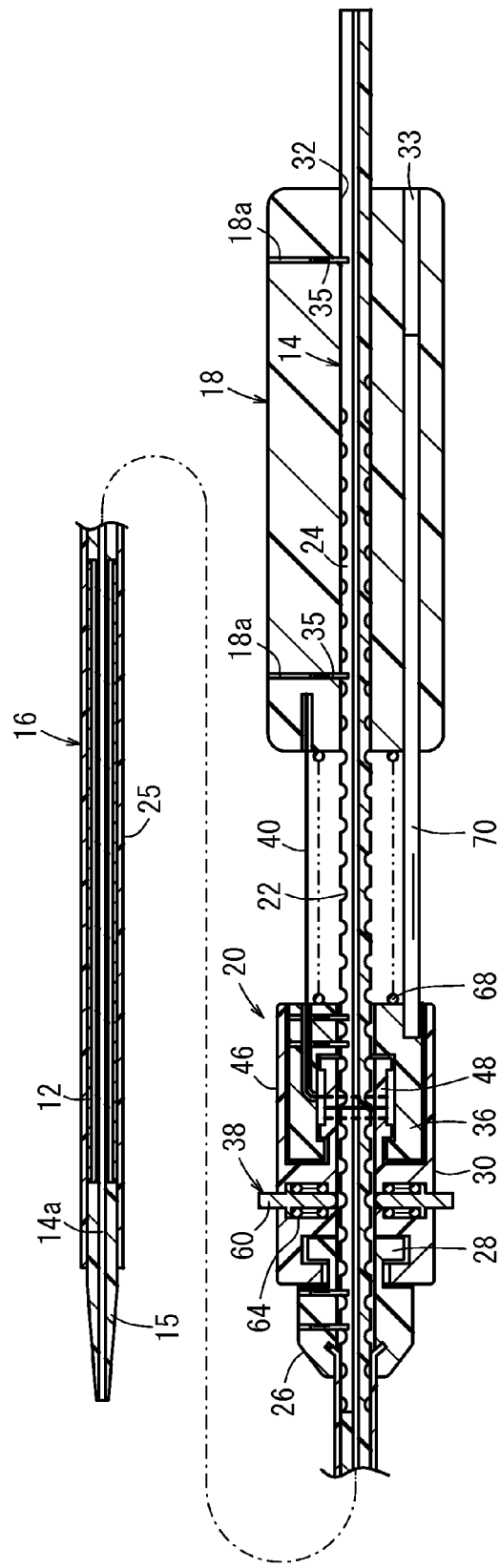
FIG. 2 is a partially omitted longitudinal cross-sectional view illustrating the stent graft delivery device of FIG. 1.

FIG. 1 is a partially omitted perspective view illustrating the stent graft delivery device 10 (hereinafter, simply referred to as a "delivery device 10") according to an exemplary embodiment of the disclosure herein. In FIG. 1, for convenience of understanding, the middle portion (between the distal side portion and the proximal side portion) in the longitudinal direction of the long delivery device 10 is partially omitted. FIG. 2 is a partially omitted longitudinal cross-sectional view illustrating the delivery device 10.

The delivery device 10 is a medical device for treating a lesion portion by allowing a stent graft 12 placed and accommodated (mounted) on the distal side to reach the lesion portion (portion to be treated), such as an aortic aneurysm, through a blood vessel, and by deploying and indwelling the stent graft 12. In addition, hereinafter, for description, the right side (a handle 18 side) of the delivery device 10 in FIG. 1 is referred to as the "proximal (rear end)" side, and the left side (the stent graft 12 side) of the delivery device 10 is referred to as the "distal" side.

The delivery device 10 includes the stent graft 12, a long shaft 14 on which the stent graft 12 is placed, a tubular sheath 16 which is slidable in the axial direction with respect to the shaft 14 and accommodates the stent graft 12, a handle 18 which is provided on the proximal side of the shaft 14 and the sheath 16, and an operation unit 20 which is provided in a position separated from the handle 18 in the axial direction.

The stent graft 12 which is delivered and indwelled in a living body has a self-expanding function. In general, a stent graft 12 having a configuration in which a stent 12b (see FIG. 6B) which is a metal skeleton (frame) for expansion is fixed on the inner surface or the outer surface of a tubular graft 12a (see FIG. 6B) can be used.

Figure 3:
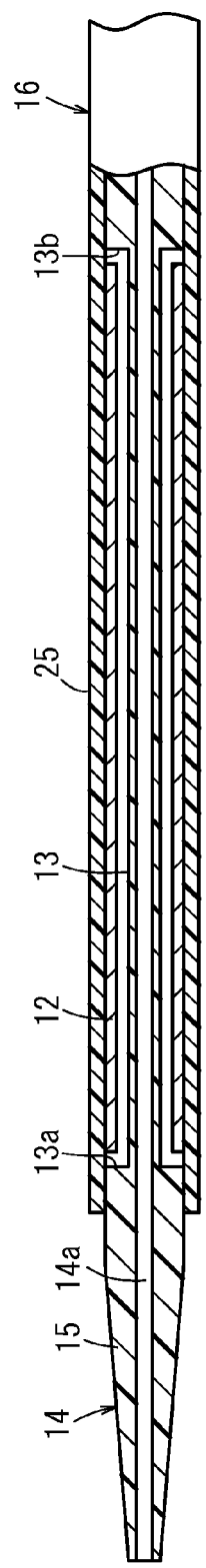
FIG. 3 is a partially omitted cross-sectional view illustrating a shaft, a distal portion of a sheath, and the vicinity thereof in an initial state (state of mounting the stent graft on the shaft).

In FIG. 3, the stent graft 12 is in a state (contracted state) in which the stent graft is accommodated in a storage space formed by the sheath 16 and a mounting portion 13 provided in the shaft 14 and the stent graft 12 is folded (i.e., compressed) since the expansion thereof is restricted. The stent graft 12 is expanded and deployed by the self-expanding function when the sheath 16 moves backward with respect to the shaft 14 and the stent graft 12 accommodated inside of the storage space is released from the restriction by the sheath 16.

The tubular graft 12a may be formed of a cloth (fabric) woven into a tubular shape by threads of a resin such as polyester or a film of ePTFE (stretched polytetrafluoroethylene), for example. The stent 12b may include a plurality of skeletons (frames) defined by a wire formed of an alloy with superelasticity such as a Ti—Ni alloy or the like in a circular shape or a Z shape. The plurality of skeletons (frames) are arranged in the axial direction of the graft 12a or a wire formed of an alloy with superelasticity or the like is knitted into a mesh shape.

As shown in FIG. 3, the shaft 14 is an elastic tubular member having flexibility formed by a guide wire lumen 14a, into which a guide wire 74 (see FIG. 6A) can be inserted, and penetrate over the entire length thereof. A tapered nose portion 15 (nose cone) is provided at the distal of the shaft 14. A mounting portion 13 for placing (mounting) the stent graft 12 is provided in the vicinity of the distal portion of the shaft 14, that is, at the proximal side of the nose portion 15. The mounting portion 13 can position and hold the stent graft 12 in a diameter-reduced state by the sheath 16 and in the axial direction by a front wall 13a forming steps on the distal side and a rear wall 13b forming steps on the proximal side.

As shown in FIGS. 1 and 2, a spiral groove 22 is provided in a predetermined range of the outer peripheral portion on the proximal side of the shaft 14. The spiral groove 22 is a recessed groove spirally extending over the predetermined range in the axial direction in the outer peripheral portion of the shaft 14. In addition, a guide unit 24 intersecting the spiral groove 22 and extending in the axial direction is provided in the predetermined range of the outer peripheral portion on the proximal side of the shaft 14. In the exemplary embodiment as illustrated, the guide unit 24 is formed in a slit shape communicating in and out of the shaft 14 in the radial direction, but a guide unit 24 having a groove shape (a recessed shape having a bottom portion) which extends in the axial direction in the outer peripheral portion of the shaft 14 may also be provided instead of the slit-shaped guide unit 24.

The guide unit 24 in the exemplary embodiment reaches (opens on the proximal surface of the shaft 14) the proximal portion of the shaft 14, but the guide unit 24 may be extended to a further position on the distal side than on the proximal of the shaft 14.

The sheath 16 includes a sheath main body 25 which is slidable in the axial direction of the shaft 14 on the outer side of the shaft 14 and a sheath hub 26 which is connected to the proximal portion of the sheath main body 25 and has a diameter greater than that of the sheath main body 25. The sheath 16 is integrally displaceable in the axial direction with respect to the shaft 14. The sheath main body 25 is a thin and elastic tubular member with flexibility which is slidably arranged in the axial direction on the outer surface side of the shaft 14.

The sheath hub 26 is provided with a circular flange portion 28 which is projected outward in the radial direction on the proximal side. The flange portion 28 is engaged with a rotating member 30 of the operation unit 20 in a relatively rotatable manner around an axis, as described below.

Figure 4:
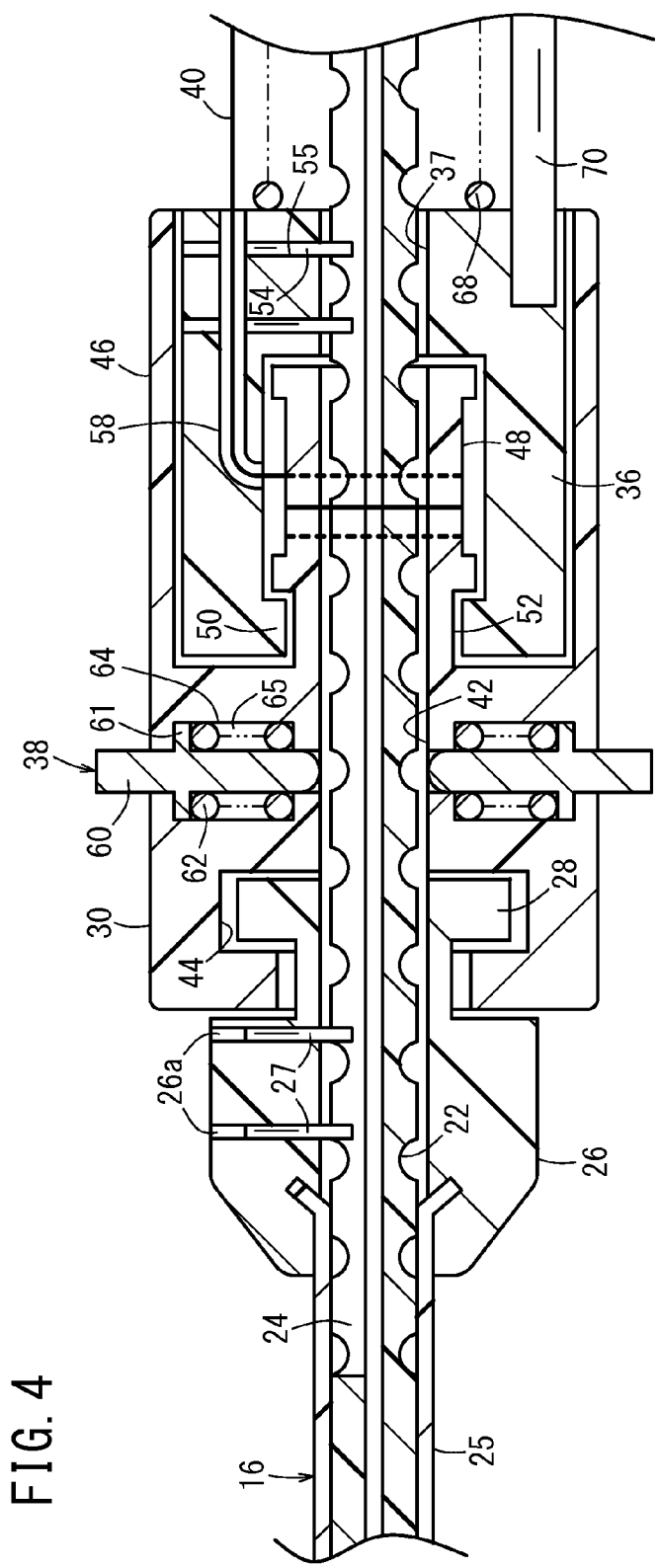
FIG. 4 is a longitudinal cross-sectional view illustrating an operation unit and the vicinity thereof in a state in which a switch member and a spiral groove are not engaged with each other.

As shown in FIG. 4, the sheath hub 26 is provided with an anti-rotation pin 27 (rotation preventing means) inhibiting relative rotation of the sheath 16 containing the sheath hub 26 with respect to the shaft 14. In the exemplary embodiment, a plurality of the anti-rotation pins 27 are provided in the axial direction at spaced intervals, but it is enough to provide only one anti-rotation pin 27. The respective anti-rotation pins 27 are held (fixed) by a holding hole 26a provided in the sheath hub 26 in a state in which one end portion of the anti-rotation pin 27 is projected into a hollow portion of the sheath hub 26. The one end portion of the anti-rotation pin 27 projected in the hollow portion of the sheath hub 26 is thus engaged with the guide unit 24 provided on the shaft 14. The sheath 16 containing the sheath hub 26 is rotatably movable in the axial direction with respect to the shaft 14 by the engagement between the anti-rotation pin 27 and the guide unit 24, but the relative rotation about the axis with respect to the shaft 14 is inhibited.

In addition, the rotation preventing means inhibiting the relative rotation of the sheath 16 and the shaft 14 is not limited to the aforesaid anti-rotation pin 27, and, for example, may have a configuration in which a projection is integrally provided on the inner periphery portion of the sheath hub 26 and engaged with the guide unit 24.

A construction material of the shaft 14 and the sheath 16 is not particularly limited, and examples thereof may include a polymer material such as a polyolefin (for example, a polyethylene, a polypropylene, a polybutene, an ethylene-propylene copolymer, an ethylene-vinyl acetate copolymer, an ionomer, or a mixture of two or more kinds thereof), a polyvinyl chloride, a polyamide, a polyamide elastomer, a polyurethane, a polyurethane elastomer, a polyester, a polyester elastomer, a polyimide, or a fluorine resin; and a mixture thereof; and a multilayer tube with two or more kinds of the aforesaid polymer materials.

The handle 18 constituting the proximal portion of the delivery device 10 is a portion gripped by a user and a cylindrical member having a length and an outer diameter suitable for easy gripping. As shown in FIGS. 1 and 2, the handle 18 is provided with an insertion hole 32 into which the shaft 14 is slidably inserted and a guide hole 33 into which a rod 70 is slidably inserted, in parallel with each other in the axial direction. In the exemplary embodiment, both ends of the insertion hole 32 are open, but the proximal side may be closed depending on the length of the shaft 14 to be inserted. In the exemplary embodiment, both ends of the guide hole 33 are also open, but the proximal side may be closed depending on the length of the rod 70 to be inserted.

An anti-rotation pin 35 (rotation preventing means) which inhibits the relative rotation of the handle 18 and the shaft 14 is further provided on the handle 18. In the exemplary embodiment, a plurality of the anti-rotation pins 35 are provided in the axial direction at spaced intervals, but only one anti-rotation pin 35 may be provided. The respective anti-rotation pins 35 are held (fixed) by a holding hole 18a provided on the handle 18 in a state in which one end portion of the anti-rotation pin is projected into the insertion hole 32 of the handle 18. One end portion of the anti-rotation pin 35 projected into the insertion hole 32 is engaged with the guide unit 24 provided on the shaft 14. The shaft 14 is relatively movable in the axial direction with respect to the handle 18 by the engagement between the anti-rotation pin 35 and the guide unit 24, but the relative rotation around the axis with respect to the handle 18 is inhibited.

In addition, the anti-rotation means inhibiting the relative rotation of the handle 18 and the shaft 14 is not particularly limited to the aforesaid anti-rotation pin 35, and, for example, may have a configuration in which a projection is integrally provided in the inner periphery portion of the handle 18 and engaged with the guide unit 24.

The relative displacement resistance between the handle 18 and the shaft 14 is greater than the friction resistance between the sheath 16 and the stent graft 12. Specifically, the relative displacement resistance between the handle 18 and the shaft 14 becomes greater than the friction resistance between the sheath 16 and the stent graft 12 by setting the thickness (outer diameter) of the anti-rotation pin 35 approximately the same as the width of the guide unit 24 provided on the handle 18 or greater than the width thereof. Due to this configuration, the shaft 14 can be prevented from moving in the proximal direction together with the sheath 16 while the sheath 16 is allowed to move in the proximal direction with respect to the handle 18.

In regard to the shaft 14 and the sheath 16, the shaft 14 is movably supported in the distal direction (distal direction) and the sheath 16 is movably supported in the proximal direction (proximal direction) from the initial position (position before starting to use) shown in FIG. 1 using the position of the handle 18 as a reference.

In addition, the shaft 14 is arranged on the most proximal side in the movable range and the sheath 16 is arranged on the most distal side in the movable range using the position of the handle 18 as a reference at the initial position shown in FIG. 1. Further, in the delivery device 10, the sheath main body 25 of the sheath 16 completely covers the mounting portion 13 of the shaft 14 and accommodates the stent graft 12 arranged in the mounting portion 13 by contracting the whole length thereof in the initial position.

The movable range of the sheath 16 with respect to the shaft 14 is set such that the most distal portion of the sheath 16 is positioned further on the proximal side than the rear wall 13b of the mounting portion 13 provided on the shaft 14 and the stent graft 12 can be completely extracted when the sheath 16 is displaced to the most proximal side.

In the exemplary embodiment, the operation unit 20 is arranged to be displaceable in the axial direction with respect to the shaft 14 further on the distal side than the handle 18. As shown in FIG. 4, the operation unit 20 includes the rotating member 30 which is relatively movable with respect to the shaft 14 and the sheath 16 and which is connected to the sheath 16; a guide member 36 which is connected to the rotating member 30 in a relatively rotatable manner and which is not relatively rotatable with respect to the shaft 14; and a switch mechanism 38 which is provided in the rotating member 30, and which permits an operator (user) to perform a switching operation. At least the sheath 16 from among the shaft 14 and the sheath 16 is driven in the proximal direction by the operation of the operation unit 20.

The operation unit 20 can switch states between a first state (non-interlocking state) in which only the sheath 16 from among the shaft 14 and the sheath 16 is allowed to be moved in the axial direction (basically proximal direction) with respect to the handle 18 while being operated by the operation unit 20 and a second state (interlocking state) in which the shaft 14 and the sheath 16 are allowed to be moved in directions opposite to each other with respect to the handle 18 while being operated by the operation unit 20 due to the action of the switch mechanism 38.

The rotating member 30 includes an axial passage opening or hole 42, into which the shaft 14 is slidably inserted; an annular concave portion 44 provided on the distal side of the rotating member 30; an outer cylinder portion 46 provided on the proximal side of the rotating member 30; and a hollow cylindrical bobbin portion 48 concentrically projecting in the proximal direction with the outer cylinder portion 46 in the outer cylinder portion 46. The sheath hub 26 and the rotating member 30 are relatively rotatable around the axis and are not relatively movable in the axial direction due to the engagement of the flange portion 28 and the annular concave portion 44.

An end of a linear member 40 is fixed to and wound around the bobbin portion 48. The linear member 40 is a member stretched between the handle 18 and the operation unit 20 with flexibility. One end thereof is wound around the rotating member 30 and another end is fixed to the handle 18. A portion of the linear member 40 between the guide member 36 and the handle 18 extends in parallel with the shaft 14. The linear member 40 is formed of metal or resin wire, or threads, for example.

The guide member 36 is a hollow cylindrical member arranged so as to cover the bobbin portion 48 in the outer cylinder portion 46. An annular convex portion 50 projecting inwardly is provided on the distal inner peripheral portion of the guide member 36. The rotating member 30 and the guide member 36 are relatively rotatable around the axis and are not relatively movable in the axial direction due to engagement of the annular convex portion 50 of the guide member 36 and the annular concave portion 52 provided on the distal side outer peripheral portion of the bobbin portion 48.

The guide member 36 is provided with an anti-rotation pin 54 (rotation preventing means) inhibiting the relative rotation of the guide member 36 and the shaft 14. In the exemplary embodiment, a plurality of the anti-rotation pins 54 are provided in the axial direction at spaced intervals, but only one anti-rotation pin 54 may be provided. The respective anti-rotation pins 54 are held (fixed) by a holding hole 55 provided in the guide member 36 in a state in which one end portion projects to a penetrating hole 37 of the guide member 36. One end portion of the anti-rotation pin 54 projected into the penetrating hole 37 is engaged with the guide unit 24 provided on the shaft 14. The operation unit 20 including the guide member 36 is relatively movable in the axial direction with respect to the shaft 14, but the relative rotation around the axis is inhibited with respect to the shaft 14 by engaging the anti-rotation pin 54 with the guide unit 24.

In addition, the anti-rotation means which inhibits the relative rotation of the guide member 36 and the shaft 14 is not particularly limited to the aforesaid anti-rotation pin 54, and, for example, the anti-rotation means may have a configuration in which a projection is integrally provided on the inner peripheral portion of the guide member 36 and the projection is engaged with the guide unit 24.

The guide member 36 guides a portion of the linear member 40 between a portion wound around the rotating member 30 and a portion fixed to the handle 18. Specifically, the guide member 36 is provided with a guide hole 58 in which one end is open at a site facing the bobbin portion 48 in the inner peripheral portion of the guide member 36 and another end is open on the proximal surface of the guide member 36. A portion of the linear member 40 between a portion wound around the rotating member 30 and a portion fixed to the handle 18 is slidably guided by the guide hole 58.

In the exemplary embodiment, as shown in FIG. 4, the switch mechanism 38 includes a switch member 60 which is displaceable to a position engaged with the spiral groove 22 provided on the shaft 14 and a position separated from the spiral groove 22, and an elastic member 62 (second biasing member) biasing the switch member 60 in a direction separating the switch member 60 from the spiral groove 22. The switch member 60 includes a pin-shaped (rod-shaped) flange portion 61 projecting outwardly in the longitudinal direction. The rotating member 30 is provided with a hole portion 64 formed between the inner peripheral portion and the outer peripheral portion in the radial direction. A diameter expanding unit 65 is provided on the middle portion of the rotating member 30 in the radial direction of the hole portion 64. The flange portion 61 of the switch member 60 is movable in the radial direction of the rotating member 30 in the diameter expanding unit 65.

Figure 5:
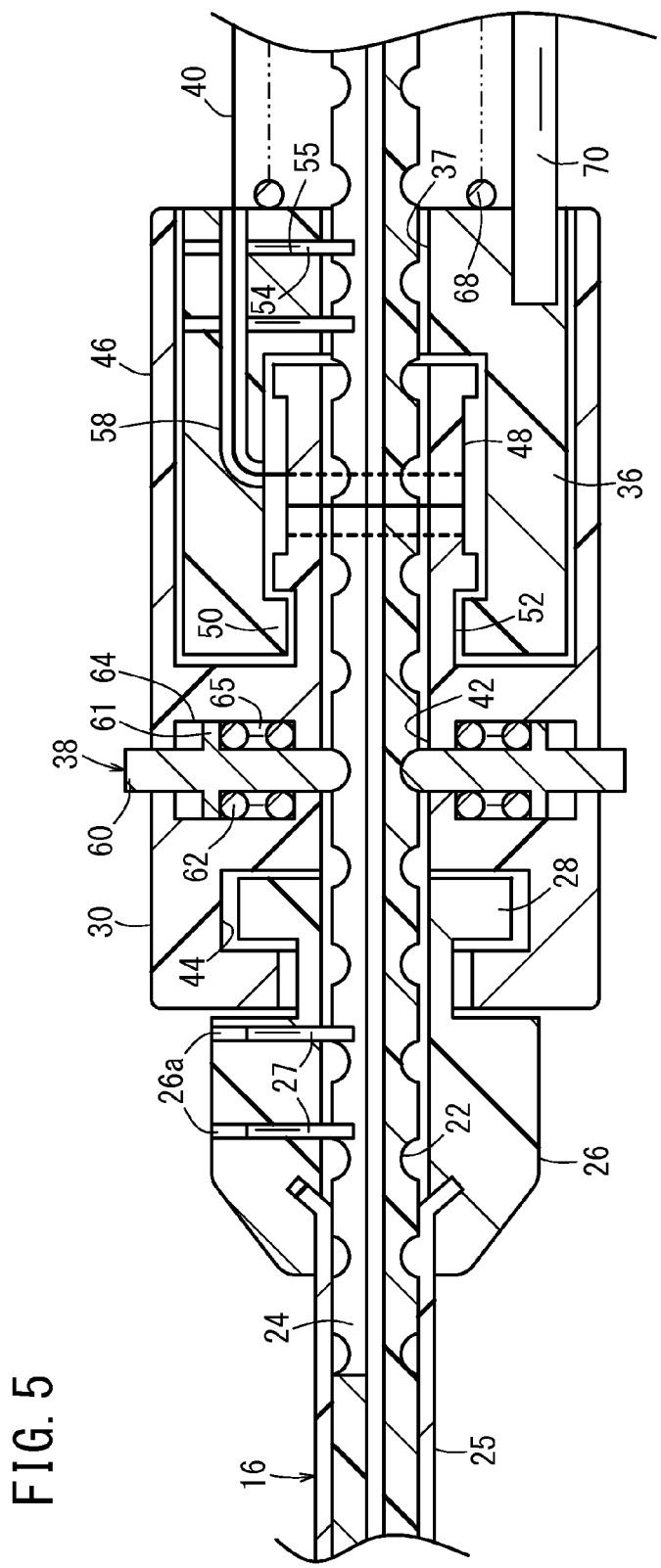
FIG. 5 is a longitudinal cross-sectional view illustrating the operation unit and the vicinity thereof in a state in which the switch member and the spiral groove are engaged with each other.

The elastic member 62 is arranged in the diameter expanding unit 65, one end thereof is brought into contact with the flange portion 61, and the switch member 60 is constantly and elastically pushed outwardly in the radial direction. Accordingly, when the switch member 60 is pushed inward with a force greater than the elastic force of the elastic member 62 from the outside of the rotating member 30, the switch member 60 moves inward in the radial direction as shown in FIG. 5. When the pushing with respect to the switch member 60 is released, the switch member 60 is returned to a position shown in FIG. 4 due to the elastic force of the elastic member 62. The elastic member 62 in the exemplary embodiment is a coiled compression spring. When the rotating member 30 rotates around the axis with respect to the shaft 14, the switch member 60 also rotates around the axis of the shaft 14 integrally with the rotating member 30.

As shown in FIG. 4, one end (outer end) of the switch member 60 projects from the outer peripheral portion of the rotating member 30 and another end (inner end) of the switch member 60 is separated from the spiral groove 22 provided on the shaft 14 in a state of not pushing the switch member 60 from the outside. In other words, the switch member 60 and the spiral groove 22 are in the non-engaged state. When the rotating member 30 is operated to rotate in a predetermined direction with respect to the handle 18 in this non-engaged state, the distance between the handle 18 and the operation unit 20 containing the rotating member 30 becomes smaller and the sheath 16 connected to the operation unit 20 is moved in the proximal direction with respect to the handle 18 by the linear member 40 being wound around the bobbin portion 48.

In contrast, as shown in FIG. 5, the another end (inner end) of the switch member 60 is engaged with the spiral groove 22 provided on the shaft 14 in a state in which the switch member 60 is pushed from the outside and displaced inward (inward in the radial direction). The switch member 60 and the spiral groove 22 function as a feed screw mechanism which allows the shaft 14 to be moved in the axial direction with respect to the operation unit 20 by engaging the switch member 60 with the spiral groove 22. Consequently, when the switch member 60 and the spiral groove 22 are in an engaged state and the rotating member 30 is operated to rotate in the predetermined direction with respect to the handle 18, the sheath 16 moves in the proximal direction with respect to the handle 18 and the shaft 14 moves in the distal direction with respect to the handle 18.

In the exemplary embodiment, the switch mechanism 38 includes multiple pairs of the switch member 60 and the elastic member 62 in the circumferential direction in the operation unit 20 at spaced intervals (in the example of the figure, two pairs in the opposite position using the axial line of the rotating member 30 as a reference). According to this configuration, as shown in FIG. 5, when one switch member 60 is in a position to be inserted into the guide unit 24 of the shaft 14, another switch member 60 is necessarily engaged with the spiral groove 22 when all the switch members 60 are pushed inward.

In the exemplary embodiment, as shown in FIGS. 1 and 2, an elastic member 68 (first biasing member) which biases the operation unit 20 in a direction separating the operation unit 20 from the handle 18 is provided between the handle 18 and the operation unit 20. The elastic member 68 is formed of a coiled compression spring as shown in the example of the figure, and is arranged on the outer side of the shaft 14 between the operation unit 20 and the handle 18. More specifically, one end of the elastic member 68 is brought into contact with the proximal surface of the guide member 36 and another end is brought into contact with the distal surface of the handle 18. The rotating member 30 is rotatable with respect to the shaft 14 and the handle 18, but the guide member 36 does not rotate with respect to the shaft 14. Therefore, even when the rotating member 30 is operated to rotate, the elastic member 68 arranged in a state of being interposed between the guide member 36 and the handle 18 is not twisted. Alternatively, the elastic member 68 may not be present.

In the exemplary embodiment, the delivery device 10 further includes the rod 70 (intermediate member) extending along with the shaft 14. The distal side of the rod 70 is fixed to the guide member 36 and the proximal side thereof is slidably inserted into the guide hole 33 provided on the handle 18. Such a rod 70 functions as a rotation preventing means inhibiting the relative rotation of the guide unit 24 and the handle 18. Since the rod 70 is slidable in the axial direction in the guide hole 33, the handle 18 and the guide member 36 are relatively displaceable in the axial direction in a state in which the relative rotation thereof is inhibited by the rod 70. In addition, since the guide member 36 is prevented from relatively rotating with the shaft 14 due to the engagement action between the anti-rotation pin 35 and the guide unit 24, the rod 70 may not necessarily be provided. Alternatively, since the relative rotation of the shaft 14 and the guide member 36 is inhibited by the rod 70 through the handle 18, the anti-rotation pin 35 may not necessarily be provided when the rod 70 is provided.

The delivery device 10 according to the exemplary embodiment is basically formed as described above, and the action and the effects thereof will be described below.

In regard to the delivery device 10 formed as described above, an action in which, without moving the shaft 14 in the distal direction with respect to the handle 18, the sheath 16 is allowed to be moved in the proximal direction (moved backward) with respect to the handle 18, and the stent graft 12 accommodated on the distal side in a diameter-reduced state is deployed and indwelled in a body cavity at the original length will be described. That is, a normal operation in which the stent graft 12 is deployed at the length according to the designed specification and indwelled in a blood vessel or the like, will be described. Further, the normal operation below will be mainly described with reference to FIGS. 6A and 6B and also appropriately described with reference to other figures (FIG. 1 or the like).

When the normal operation is performed, firstly, the mode of a lesion portion such as an aneurysm generated in an aorta or the like is specified by an intravascular contrast method or an intravascular ultrasound diagnosis method. Next, as shown in FIG. 6A, the guide wire 74 is introduced by being advanced into a blood vessel 72 from a thigh portion or the like by, for example, a seldinger or other known method. The guide wire 74 is inserted into the proximal side from the distal side of the guide wire lumen 14*a* of the shaft 14 (see FIG. 2), and the shaft 14 and the sheath 16 are inserted into an aorta. Moreover, under the X-ray contrast using an X-ray opaque marker (not illustrated) provided on the distal side of the shaft 14 and the sheath 16, the stent graft 12 which is accommodated on the distal side of the sheath 16 is delivered to a target position.

The state of the delivery device 10 shown in FIG. 6A enters the initial state in which the sheath 16 is positioned on the most distal side in the movable range with respect to the handle 18 (see FIG. 1), and the stent graft 12 is completely accommodated on the distal side of the sheath main body 25. In a state in which the switch member 60 is not operated from the initial state, that is, in a state in which the switch member 60 is not pushed inward (see FIG. 4), the operation unit 20 containing the rotating member 30 is moved toward the handle 18 side by winding the linear member 40 around the bobbin portion 48 when the rotating member 30 is gripped and is allowed to rotate in the predetermined direction around the axis with respect to the handle 18 and the shaft 14. As shown in FIG. 6B, the sheath 16 connected to the rotating member 30 is moved in the proximal direction in this way.

At this time, since the relative movement in the axial direction between the handle 18 and the shaft 14 is restricted to a certain extent by an engaging force (friction resistance) between the anti-rotation pin 35 provided on the handle 18 and the guide unit 24 provided on the shaft 14, the shaft 14 is not displaced in the proximal direction with respect to the handle 18 together with the sheath 16 due to the friction resistance between the sheath 16 and the stent graft 12 when the sheath 16 is moved in the proximal direction.

In the case of the exemplary embodiment, since the elastic member 68 (see FIG. 1) biasing the operation unit 20 in a direction separating the operation unit 20 from the handle 18 is provided, the tension strength is applied to the linear member 40 by the elastic force of the elastic member 68. Therefore, the distance between the handle 18 and the operation unit 20 is reliably held at the distance prescribed by the linear member 40.

Further, since the sheath hub 26 is rotatably engaged with the rotating member 30 and the relative rotation around the axis with respect to the shaft 14 is inhibited, the sheath 16 does not rotate along with the rotation operation with respect to the rotating member 30.

With the switch member 60 being elastically biased outwardly in the radial direction by the elastic member 62, the switch member 60 is held in a position separated from the spiral groove 22 as long as an operator does not operate the switch member 60 by pushing inward. Accordingly, using the handle 18 as a reference, an operation for moving the sheath 16 in the proximal direction can be reliably performed without moving the shaft 14 in the distal direction.

The stent graft 12 which is restricted from expanding (deploying) in the main body of the sheath 16 is deployed by the self-expansion function in the blood vessel 72 by the release of the restriction in the process of the shaft 14 being moved in the proximal direction with respect to the sheath 16. Further, when the distal end of the sheath 16 (sheath main body 25) reaches a position further on the proximal side than the proximal end of the stent graft 12, the stent graft 12 enters a complete deploying state over the entire length thereof. FIG. 6B illustrates the complete deploying state of the stent graft 12. The stent graft 12 can be indwelled in the blood vessel 72 at the original length L1 by the above-described operation.

Next, in regard to the delivery device 10, an action in which the shaft 14 is moved (advanced) in the distal direction with respect to the handle 18 at the same time that the sheath 16 is moved (retreated) in the proximal direction with respect to the handle 18, and the stent graft 12 accommodated on the distal side in the diameter-reduced state is indwelled and deployed to be shorter than the original length L1 in a body cavity will be described. That is, a shortening operation in which the stent graft 12 is deployed at a length shorter than the designed specification and indwelled in a blood vessel or the like will be described. Further, the shortening operation below will be mainly described with reference to FIGS. 7A and 7B and also appropriately described with reference to other figures (FIG. 1 or the like).

The shortening operation is performed when, for example, the stent graft 12 with a specification longer than a predicted length is deployed and indwelled while being contracted because a length necessary for indwelling cannot be precisely predicted with an X-ray contrast image or a CT image acquired before surgery due to a blood vessel having a plurality of bent sections.

Firstly, as shown in FIG. 7A, in the same manner as in the normal operation, the shaft 14 and the sheath 16 are inserted into an aorta and are delivered to a target position which is the distal side (position accommodating the stent graft 12) of the shaft 14 and the sheath 16 in a state in which the guide wire 74 is advanced. Further, the switch member 60 of the switch mechanism 38 is operated to be pushed inward from the outside of the rotating member 30 and an inward end of the switch member 60 is inserted (interlocked) into the spiral groove 22 (see FIG. 5). That is, the switch member 60 and the spiral groove 22 are in an engaged state.

Subsequently, the rotating member 30 is gripped and rotated in the predetermined direction while the engaged state between the switch member 60 and the spiral groove 22 is maintained. In this way, the operation unit 20 containing the rotating member 30 is moved to the handle 18 side by winding the linear member 40 around the bobbin portion 48 of the rotating member 30, and the shaft 14 moves in the distal direction with respect to the operation unit 20 by the action of the feed screw mechanism formed by engaging the switch member 60 with the spiral groove 22.

At this time, the stent graft 12 is deployed by moving the sheath 16 in the proximal direction at the same time that the stent graft 12 accommodated in the sheath 16 is extracted by the shaft 14 moving in the distal direction. As a result, a length by which the stent graft 12 is extracted from the sheath 16 is longer than a length by which the sheath 16 is moved in the proximal direction, and the deploying and indwelling are completed with a length L2 shorter than the original length L1 (see FIG. 6B) in a body cavity as shown in FIG. 7B.

According to the delivery device 10 as described above, the entire length of the stent graft 12 can be simply and reliably shortened by moving the shaft 14 in the distal direction with respect to the handle 18 in a state of holding the position of the handle 18 when the sheath 16 is moved in the proximal direction with respect to the handle 18 to expand and deploy the stent graft 12. Accordingly, a technique of easily shortening the entire length of the stent graft 12 with less dependence on the expertise and/or technique of the operator when compared with the technique of shortening the entire length of the stent graft 12 by pushing up the entire delivery device 10 as in the related prior art can be performed.

In the case of the exemplary embodiment, the sheath 16 is moved in the proximal direction with respect to the handle 18 at the same time that the shaft 14 is automatically moved in the distal direction by the action of the feed screw mechanism formed by the switch member 60 and the spiral groove 22 along with the operation for rotating the rotating member 30 in the predetermined direction in a state of pushing the switch member 60 inward. Therefore, the technique for shortening the stent graft 12 while expanding it can be simply and reliably performed without depending on the operator's skill.

In the case of the exemplary embodiment, since the linear member 40 is wound around the rotating member 30 along with the operation for rotating the rotating member 30 and thus the operation unit 20 is drawn into the handle 18 side, the sheath 16 can be reliably moved in the proximal direction. In addition, since the guide member 36 is provided in the rotating member 30, the operation unit 20 can be formed in a compact manner.

Because the amount of movement of the shaft 14 with respect to the amount of movement of the sheath 16 is determined by the outer diameter of the bobbin portion 48 and the pitch of the spiral groove 22 when the shaft 14 is operated to advance while the sheath 16 is retreated using the handle 18 as a reference, the amount of shaft 14 movement to the amount of sheath 16 movement can be fixed to an arbitrarily set ratio. Consequently, in the stent graft 12, the possibility that the stents 12b overlap each other or that the graft 12a is turned over can be reliably prevented.

In the exemplary embodiment, the operation unit 20 can switch states between (1) the first state (non-interlocking state) in which the sheath 16 is moved in the proximal direction with respect to the handle 18 without moving the shaft 14 in the distal direction with respect to the handle 18 when the operation unit 20 is operated and (2) the second state (interlocking state) in which the sheath 16 is moved in the proximal direction with respect to the handle 18 and the shaft 14 is moved in the distal direction with respect to the handle 18 when the operation unit 20 is operated by operating the switch mechanism 38. Accordingly, the size of the stent graft 12 to be contracted is easily adjusted and the stent graft 12 can be indwelled in a blood vessel at an arbitrary (desired) length which is shorter than the original length, depending on the length or meandering degree of a blood vessel of a patient.

Further, in the exemplary embodiment, since the switch mechanism 38 includes the elastic member 62 which biases the switch member 60 outwardly in the radial direction of the rotating member 30, the operation unit 20 maintains the first state when the switch member 60 is not pushed in and the operation unit 20 enters the second state only when the switch member 60 is operated to be pushed in. Therefore, the switch mechanism can be smoothly and reliably switched between the first state and the second state.

In addition, by providing a plurality of the switch members 60 in the circumferential direction in the operation unit 20 at spaced intervals, another guide member 36 is necessarily engaged with the spiral groove 22 when any one of the switch members 60 is in the position to be inserted into the guide unit 24 while the rotating member 30 is operated to rotate in a state in which the switch member 60 and the spiral groove 22 are engaged with each other. Therefore, the shaft 14 may be smoothly moved forward by the rotation operation of the rotating member 30 and the operability thereof is excellent.

Figure 8:
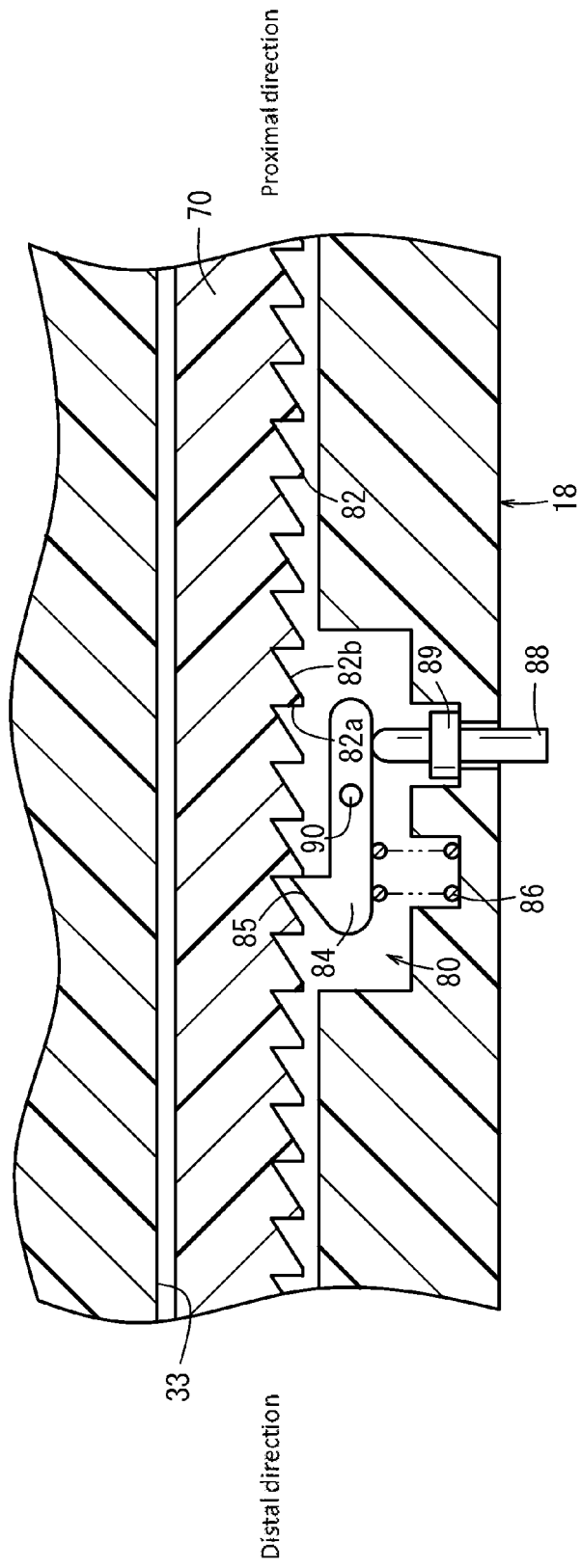
FIG. 8 is a longitudinal cross-sectional view describing a ratchet mechanism provided in a stent graft delivery device.

As shown in FIG. 8, the delivery device 10 may include a ratchet mechanism 80 (displacement restricting mechanism) which allows the rod 70 to be displaced in the proximal direction with respect to the handle 18 and which is capable of inhibiting the rod 70 from being displaced in the distal direction with respect to the handle 18.

The ratchet mechanism 80 includes a ratchet tooth 82 which is provided in the axial direction on the outer peripheral portion of the rod 70; a ratchet claw member 84 which is capable of meshing with the ratchet tooth 82; an elastic member 86 (for example, a spring member) which elastically biases the ratchet claw member 84 in a direction of pushing the ratchet claw member 84 to the ratchet tooth 82; and a restriction release unit 88 which releases the engagement between the ratchet tooth 82 and the ratchet claw member 84.

The ratchet tooth 82 is formed of a vertical surface 82a which is vertical with respect to the axis line of the shaft 14 and an inclined surface 82b inclining outwardly toward in the distal direction of the shaft 14. A claw portion 85 which can be engaged with the ratchet tooth 82 is provided on one end of the ratchet claw member 84, and the intermediate portion in the longitudinal direction is rotatably supported by an axis portion 90. In the elastic member 86, one end is attached to a wall in the handle 18 and another end is attached to the ratchet claw member 84, and the ratchet claw member 84 is pushed toward the shaft 14 side.

The restriction release unit 88 is movably provided in the radial direction of the handle 18 in a state of penetrating the wall portion of the handle 18. One end of the restriction release unit 88 projects to the outside of the handle 18 and another end is attached to another end side (opposite side of the claw portion 85 using the axis portion 90 as a reference) of the ratchet claw member 84. A flange portion 89 which bulges outward is provided in the intermediate portion in the longitudinal direction of the restriction release unit 88, and the restriction release unit 88 is prevented from escaping from the handle 18 by the flange portion 89 caught by the inner wall of the handle 18.

In the ratchet mechanism 80 configured as described above, since the ratchet claw member 84 rotates in a direction in which the claw portion 85 moves away from the shaft 14 due to the taper action of the inclined surface 82b and the claw portion 85 climbs over the ratchet tooth 82, the rod 70 is allowed to move in the proximal direction with respect to the handle 18. Meanwhile, since the vertical surface 82a of the ratchet tooth 82 is engaged with the claw portion 85 of the ratchet claw member 84 under the elastic biasing action with respect to the ratchet claw member 84 of the elastic member 86, the rod 70 is inhibited from moving in the distal direction with respect to the handle 18.

In an embodiment where the ratchet mechanism 80 is not provided, when a force is applied to the operation unit 20 in a direction separating the same from the handle 18 in the operation of the delivery device 10, by the fact that the rotating member 30 rotates in a direction opposite to the direction when the sheath 16 is moved in the proximal direction and the linear member 40 wound around the bobbin portion 48 is extracted through the guide hole 58, there is a possibility that the sheath 16 may move in the distal direction with respect to the handle 18. In contrast, when the ratchet mechanism 80 is provided, the rod 70 is allowed to be displaced in the proximal direction with respect to the handle 18, but the rod 70 is inhibited from being displaced in the distal direction with respect to the handle 18, so it is possible to prevent the sheath 16 from unintentionally moving in the distal direction with respect to the handle 18.

When the restriction release unit 88 is operated to be pushed inward, the ratchet claw member 84 rotates in a direction in which the claw portion 85 moves away from the ratchet tooth 82 by the restriction release unit 88 and the engagement between the ratchet claw member 84 and the ratchet tooth 82 is released. That is, movement restriction, due to the ratchet mechanism 80, in the distal direction with respect to the rod 70 is released. The sheath 16 is movable in the distal direction when the rod 70 is movable in the distal direction with respect to the handle 18. In this way, since the movement restriction with respect to the rod 70 can be simply and rapidly released by operating the restriction release unit 88 to be pushed, the sheath 16 can be moved in the distal direction with respect to the handle 18 as needed.

The disclosure herein has been described with reference to the preferred exemplary embodiments, but the present invention is not limited thereto, and various modifications are obviously possible within the range not departing from the scope of the present invention.

The detailed description above describes a stent graft delivery device disclosed by way of example. The invention is not limited, however, to the precise exemplary embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent graft delivery device, comprising:
    a stent graft;
    a shaft on which the stent graft is placed;
    a tubular sheath which is slidable in an axial direction with respect to the shaft and accommodates the stent graft;
    a handle which is provided on a proximal side of the shaft and the sheath;
    an operation unit which is movably provided in the axial direction with respect to the shaft, in a position separated from the handle in the axial direction and which drives at least the sheath from among the shaft and the sheath; and
    a switch mechanism which is provided in the operation unit,
    wherein the shaft and the sheath are provided movable in the axis direction using the handle as a reference, and
    the state of the operation unit is switched between a first state in which only the sheath from among the shaft and the sheath is allowed to be moved in the axial direction with respect to the handle while being controlled by the operation unit and a second state in which the shaft and the sheath are allowed to be moved in directions opposite to each other with respect to the handle while being controlled by the operation unit under the switch mechanism.

2. The stent graft delivery device according to claim 1,
    wherein the operation unit includes a rotating member which is relatively rotatable with respect to the shaft and the sheath and connected to the sheath, and a guide member which is connected in a relatively rotatable manner with respect to the rotating member and is not relatively rotatable with respect to the shaft, and
    wherein the shaft and the sheath are not relatively rotatable with one another.

3. The stent graft delivery device according to claim 2, further comprising:
    a flexible linear member having an end wound around the rotating member,
    wherein another end of the linear member is fixed to the handle, and
    wherein the guide member guides a middle portion of the linear member between a portion wound around the rotating member and a portion fixed by the handle.

4. The stent graft delivery device according to claim 3,
    wherein the rotating member includes an outer cylindrical portion, and a bobbin portion which is provided in the outer cylindrical portion and the linear member wound around it, and
    the guide member is arranged so as to cover the bobbin portion in the outer cylindrical portion.

5. The stent graft delivery device according to claim 4,
    wherein the guide member is provided with a guide hole in which one end is open at a site facing the bobbin portion in an inner peripheral portion of the guide member and another end is open on a proximal surface of the guide member, and
    the middle portion of the linear member is slidably guided by the guide hole.

6. The stent graft delivery device according to claim 2, further comprising a first biasing member which biases the operation unit in a direction separating the operation unit from the handle.

7. The stent graft delivery device according to claim 6, wherein one end of the first biasing member is attached to the proximal surface of the guide member and another end is attached to a distal surface of the handle.

8. The stent graft delivery device according to claim 2, further comprising:
    an intermediate member in which one end is fixed to the guide member and another end is slidably inserted into the handle, and
    a displacement restricting mechanism which allows the intermediate member to be displaced in the proximal direction with respect to the handle and inhibits the intermediate member from being displaced in the distal direction with respect to the handle.

9. The stent graft delivery device according to claim 8, wherein the displacement restricting mechanism includes a restriction release unit which releases displacement restriction with respect to the intermediate member.

10. The stent graft delivery device according to claim 1, further comprising a spiral groove formed in an outer peripheral portion of the shaft, and
wherein the switch mechanism includes a switch member which is displaceable between a position engaged with the spiral groove and a position separated from the spiral groove.

11. The stent graft delivery device according to claim 10, wherein the switch mechanism includes a second biasing member which biases the switch member in a direction separating the switch member from the spiral groove, and
wherein the switch member is engaged with the spiral groove when a pushing operation is performed on the switch member.

12. The stent graft delivery device according to claim 10, wherein the shaft is provided with a slit-shaped or a groove-shaped guide unit which intersects the spiral groove and extends in the axial direction, and
wherein a plurality of the switch members are provided in the circumferential direction in the operation unit at intervals.

13. The stent graft delivery device according to claim 1, wherein relative displacement resistance between the handle and the shaft is greater than friction resistance between the sheath and the stent graft.

14. The stent graft delivery device according to claim 1, wherein the stent graft is indwelled at an original length when the operation unit is in the first state and wherein the stent graft is indwelled at an arbitrary length shorter than the original length when the operation unit is in the second state.

15. The stent graft delivery device according to claim 1, wherein the stent graft is self-expanding.

16. The stent graft delivery device according to claim 1, wherein the tubular sheath includes a sheath hub, the sheath hub including rotation preventing means for inhibiting relative rotation of the sheath with respect to the shaft.

17. The stent graft delivery device according to claim 1, wherein the handle includes a rotation preventing means for inhibiting the relative rotation of the handle with respect to the shaft.

18. The stent graft delivery device according to claim 1, wherein, when the operation unit is in the first state, the sheath is permitted to move in the axial direction relative to the handle and, when the operation is in the second state, the sheath and the shaft are permitted to move in the axial direction relative to the handle.

19. The stent graft delivery device according to claim 18, wherein, when the operation unit is in the first state, the sheath is permitted to move in a proximal direction relative to the handle and, when the operation unit is in the second state, the sheath and the shaft are permitted to move in directions opposite to each other relative to the handle, the sheath moving in a proximal direction and the shaft moving in a distal direction.

20. The stent graft delivery device according to claim 1,
wherein the operation unit includes a rotating member which is rotatable with respect to the shaft and the sheath, and which is connected to the sheath;
wherein the shaft includes a spiral groove formed in an outer peripheral portion thereof, the switch mechanism including a switch member which is displaceable between a position engaged with the spiral groove and a position separated from the spiral groove; and
wherein, when the rotating member rotates about an axis with respect to the shaft, the switch member also rotates about the axis of the shaft integrally with the rotating member.

* * * * *